United States Patent [19]
Moritani et al.

[11] Patent Number: 5,948,632
[45] Date of Patent: *Sep. 7, 1999

[54] METHOD AND REAGENT FOR MEASURING CHLORINE AND CALCIUM IONS USING A MALTOSE DERIVATIVE

[75] Inventors: Yukako Moritani, Osaka; Setsuko Takahata, Shiga-ken, both of Japan; Masashi Nakagawa, Andover, Mass.; Seiichi Kohda; Tuyosi Fujita, both of Osaka, Japan

[73] Assignee: Oriental Yeast Co., Ltd., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/757,845

[22] Filed: Nov. 27, 1996

[30] Foreign Application Priority Data

Nov. 28, 1995 [JP] Japan ................................. 7-331232
Nov. 28, 1995 [JP] Japan ................................. 7-331233

[51] Int. Cl.⁶ ........................................ C12Q 1/40
[52] U.S. Cl. ............................ 435/22; 435/18; 435/962
[58] Field of Search ............................ 435/14, 18, 22, 435/25, 962; 436/79; 536/4.1

[56] References Cited

U.S. PATENT DOCUMENTS

| | | | |
|---|---|---|---|
| 5,229,270 | 7/1993 | Ono et al. | 435/22 |
| 5,384,246 | 1/1995 | Berry et al. | 435/22 |
| 5,618,684 | 4/1997 | Nonobe et al. | 435/16 |

FOREIGN PATENT DOCUMENTS

| | | |
|---|---|---|
| 0 085 348 | 8/1983 | European Pat. Off. . |
| 0 275 398 | 7/1988 | European Pat. Off. . |
| 0 486 470 | 5/1992 | European Pat. Off. . |
| 0 510 620 | 10/1992 | European Pat. Off. . |
| 62-36199 | 2/1987 | Japan . |
| 63-126497 | 5/1988 | Japan . |
| 64-2598 | 1/1989 | Japan . |
| 1-231896 | 9/1989 | Japan . |
| 61-13894 | 4/1994 | Japan . |
| WO 95/04831 | 2/1995 | WIPO . |

OTHER PUBLICATIONS

Kayamori Y., Enzymatic Method for Assaying Calcium in Serum and Urine with Porcine Pancreatic Alpha–Amylase, Clinical Chemistry 40/5 781–784, 1994.

Amylase (Edited by Onishi, Sakano and Taniguchi under the supervision of Nakamura and published Jan. 1, 1986 by Gakkai Publication Center, pp. 141–144.

Clin. Chem. 40, 1994, 781–784.

Clin. Chem 34, 1988, 2005–2008.

*Primary Examiner*—Ralph Gitomer
*Attorney, Agent, or Firm*—Nixon & Vanderhye

[57] ABSTRACT

Chlorine and calcium ions are measured in a biological sample using a maltose derivative having a chromogenic group at the reducing end. These ions are accurately measured in biological samples such as blood and urine without influence of amylase that may be present in such samples.

4 Claims, 2 Drawing Sheets

METHOD AND REAGENT FOR MEASURING CHLORINE AND CALCIUM IONS USING A MALTOSE DERIVATIVE

FIELD OF THE INVENTION

This invention relates to a method for measuring a specific type of ions, and more specifically to an enzyme assay for measuring a specific type of ions by contacting the ions in a sample with amylase which expresses its activity only in the presence of the ions, such as chlorine and calcium and measuring amylase activity varying with the levels of ions in the sample.

More specifically, the present invention relates to a method for measuring variable amylase activity by using a maltose having a chromogenic group at the reducing end (hereinafter referred to as a maltose derivative) as a measurement reagent and measuring the degradation rate or degradation degree of the maltose derivatives on the basis of released chromogenic materials.

PRIOR ART

Ions such as chlorine and calcium are known to play important roles in living bodies. However, effective measurement methods for these ions have never been developed.

For example, chlorine (also referred to as "Cl") primarily exists in extracellular fluids in human bodies in the amount of about 2000 mEq Cl per adult. The Cl level in living bodies need to be maintained within the ranges of normal Cl values, such as 97 to 103 mEq/L in serum, 122 to 132 mEq/L in medulla, 10 to 60 mEq/L in sweat, and 170 to 250 mEq/day in urine.

Once a disease has developed, the Cl level shifts. Hyperchloremia corresponding to a Cl value of 108 mEq/L or more in serum, for example, is caused by dehydration (water deficiency), overdosing of Cl agents, administration of carbonate dehydratase inhibitors, renal tubular acidosis, respiratory alkalosis hyperpnea, hyperventilation syndrome, encephalitis, empyemic fibrosis of the pancreas, hypoaldosteronism, etc.

On the other hand, hypochloremia corresponding to a Cl value of 108 mEq/L or less in serum, for example, is caused by attenuant hypochloremia, overhydration, loss of digestive fluids, renal loss, renal failure, chronic pyelitis, diuresis, dyscorticism, lobar pneumonia, pneumonectasis, disorder of respiratory centers, meningitis, etc.

Known methods for measuring chlorine ions in serum include Schales-Schales assay, electrometric titration assay, ion electrode assay, and enzyme assay. However, the electrometric titration assay and ion electrode assay require special, complex and expensive equipments such as those provided with a chloridometer or an ion selective electrode. The Schales-Schales assay needs a special attention for treating waste liquor or other processes because mercury is used as a measurement reagent.

The enzyme assay includes an assay using amylase as an enzyme. As an example, a reagent for measuring chlorine ions comprising a complexing reagent, non-active α-amylase, a calcium ion-containing complex and an α-amylase activity measuring reagent is known (Japanese Patent Public Disclosure No. 126497/88). However, it is well-known that amylase also exists in blood and considerably varies with disease conditions, individuals, time and other factors. If a chlorine level is to be determined by amylase activity, this variation of amylase activity in blood may lead to positive or negative errors in the measurement of chlorine. Amylase not only exists at a high level particularly in the blood of patients having pancreatic diseases, but also in saliva, for example, and floats as mist in the air, thereby inducing positive measurement errors.

Calcium is also an example of ions which play important roles in living bodies. Calcium is in vivo localized in bones and teeth at 99% or more, and repeatedly absorbed into and excreted from bones at about 700 mg/day. Thus, calcium also exists in body fluids and cells at lower levels than in bones. Calcium in body fluids and cells not only participates in blood coagulation but also serves as "second messenger" in other important vital functions such as neurotransmission, muscular contractile function, hormonal action, so that the calcium level in body fluids, particularly blood, must be kept strictly constant. It is known that the calcium level in blood is kept constant by vitamin D, parathyroid hormone, calcitonin or the like strictly at 9 to 11 mg/dl in normal human blood with a daily variation of at most ±3%. Once a disease has developed, a calcium level shifts. Hypercalcemia is caused by diseases such as myxedema, malignant tumor, sarcoidosis, hyperproteinemia, hyperthyroidism, while hypocalcemia is caused by diseases such as hypoparathyroidism, osteomalacia, renal rickets, uremia, hypoproteinemia, malignant tumor bone metastasis. The measurement of calcium in blood is a very important factor for clinical tests, because the calcium level in normal human blood is very strictly maintained and even a slight shift of the calcium level may readily be attributed to a disease condition.

Known methods for measuring calcium in blood include atomic absorption spectrometry, ion electrode assay, and chelatocolorimetry using a reagent such as OCPD (o-cresol phthalein complexone). However, all these methods involve many problems, e.g., atomic absorption spectrometry and ion electrode assay require complex operations and specialized and expensive equipment, and the chelatocolorimetry requires the addition of 8-oxyquinoline as a masking agent due to the low reaction specificity of OCPC to magnesium. 8-Oxyquinoline magnesium is masked to avoid positive errors, but calcium is also trapped with the result that the color development sensitivity is lowered or low levels of calcium can not be detected or other problems occur. Further, the reagent must be strictly adjusted at a proper pH level because a minor difference in pH invites a significant shift of the color development degree.

Several enzymatic assays for measuring calcium in blood using an enzyme similarly to the method of this invention have been reported. According to Japanese Patent Public Disclosure No. 36199/87, calcium in a sample is reacted with calmodulin to form a calcium-calmodulin complex. This complex is used to activate a calmodulin-dependent enzyme and the enzyme activity is measured to quantify calcium in the sample. However, it is difficult to widely apply this method, because the sample must be preliminarily diluted due to the narrow assay range and too high sensitivity and calmodulin and substrates for calmodulin-dependent enzyme are expensive and unstable. Japanese Patent Public Disclosure No. 2598/89 discloses a method for measuring calcium by adding calcium into an excess amount of oxalate and measuring the remaining precipitated oxalate by oxalic acid oxidase, but this method needs improvement in the following respects: it is a method using an operation for precipitating calcium as calcium oxalate; this method is susceptible to ascorbic acid and bilirubinic acid in the sample because oxalic acid oxidase is used for the detection; the standard curve is downward; a rate assay is not possible. Japanese Patent Public Disclosure No. 231896/89 discloses a method for measuring calcium by using phosphoryl choline thioester as a substrate to measure enzyme activity of phospholipase A2 varying with calcium level, but this method uses an SH measurement reagent such as DTNB (5,5'-dithiobis-2-nitrobenzoic acid) for the detection of enzyme activity so that it is directly exposed to the influence of a sulfur-containing compound such as cystein or protein in blood.

Recent reports include measurement methods using amylase (Reports of the 23rd Meeting of Japan Clinical Test Automation Society, Title No. 222–223). It is known that amylase expresses its activity particularly when it is bound to calcium, but can not express its activity in the absence of calcium, as described in detail in "Amylase" (edited by Onishi, Sakano and Taniguchi under the supervision of Nakamura and published Jan. 1, 1986 by Gakkai Publication Center, pp. 141–144), for example. However, amylase also exists in blood as described above, and considerably varies with the disease condition, individual, time and other factors. If a calcium level is to be measured by amylase activity, this variation of amylase activity in blood may lead to positive or negative errors in the measurement of calcium, just as with chlorine.

For example, Katayama et al. reported a method for measuring calcium in serum or urine by using 2-chloro-4-nitrophenyl-α-maltotrioside (G3CNP) represented by the following chemical formula 1:

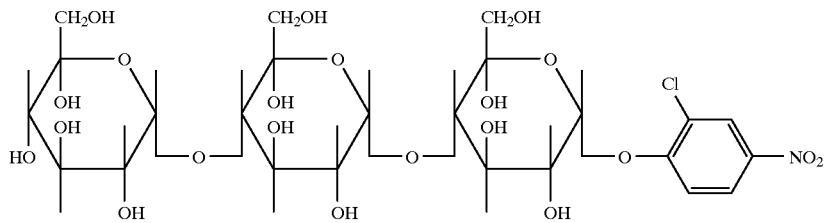

and porcine-derived amylase (Yuzo Kayamori, Yoshiaki Katayama (1994), Clin. Chem. 40, 784-784). However, the above report of Katayama et al. also shows that amylase brought from serum or the like leads to positive errors in the measurement of calcium, and more specifically, the section of "Discussion" says that the amylase level is so high in serum or urine of patients of acute splenitis or hyperamylasemia that positive errors occur.

As discussed above, the measuring method of ions such as chlorine and calcium by using the enzyme amylase. The enzyme assay is an excellent method for measuring ions as compared with the former three assays in that ions can be conveniently measured with a simpler equipment without using harmful mercury, however, it is inevitably accompanied by positive or negative errors.

SUMMARY OF THE INVENTION

It is the object of the present invention to provide a reagent for measuring a specific type of ions comprising a maltose derivative having a chromogenic group introduced into the reducing end, wherein said ions can promote hydrilysis of said maltose derivative in a dose-dependent manner.

The measurement reagent according to the present invention uses maltose derivatives and therefore, has very little susceptibility to amylase existing in serum or urine and very high reactivity to ions such as chlorine, so that ions can be directly and exactly measured in various samples even containing amylase (for example, biological samples) irrespective of the amylase contaminated in these samples, i.e. without deactivating the pre-existed amylase.

It is another object of the present invention to provide a method for measuring a specific type of ions which can promote hydrolysis of said maltose derivative in a dose-dependent manner. The measuring method of the present invention comprises reacting a sample which is supposed to contain a specific type of ions, and said measurement reagent under the existence of amylase, and measuring the concentration of the ions in said sample on the basis of quantity of free chromogenic group derived from the hydrolysis of the maltose derivative.

It is a further object of the present invention to provide a kit for measuring a specific type of ions which can promote hydrolysis of said maltose derivative in a dose-dependent manner, comprising a maltose derivative, and also the amylase protein, buffer or the like, if necessary, which are packed appropriately.

DETAILED DESCRIPTION OF THE INVENTION

Figure 1:
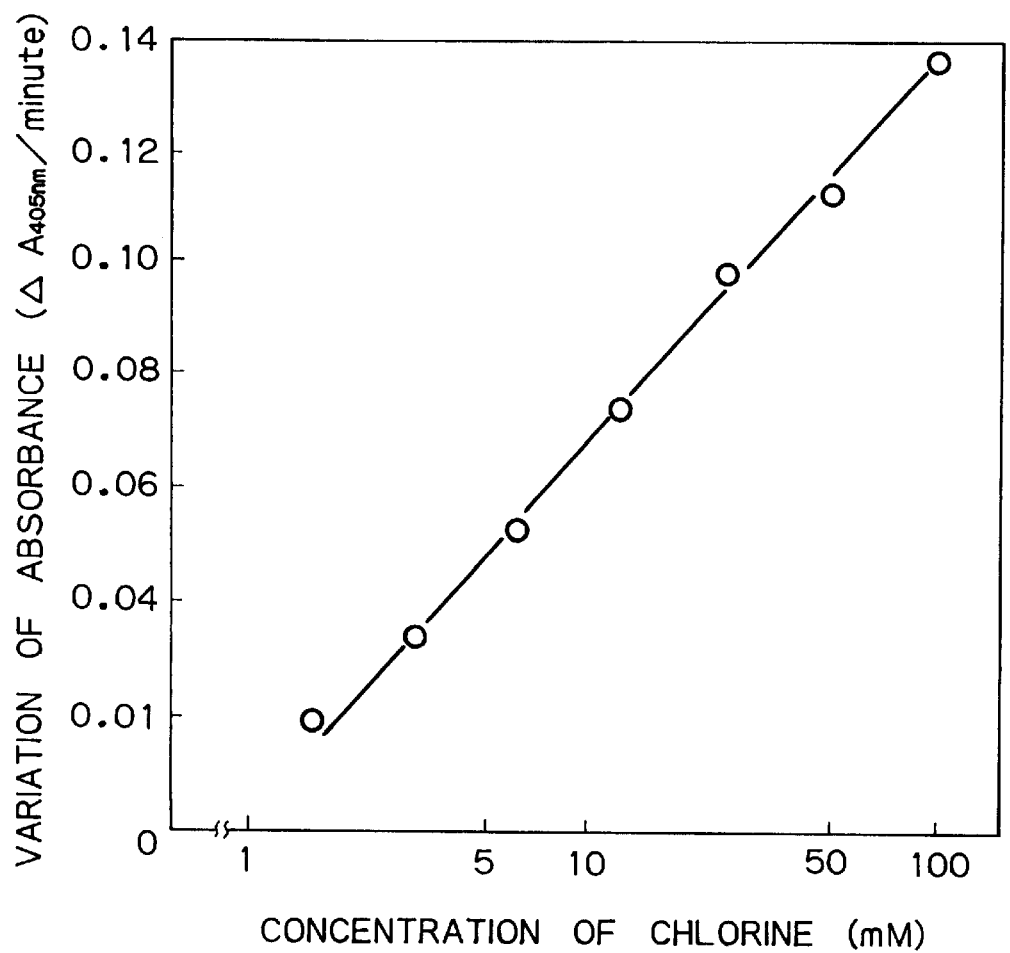
FIG. 1 shows a measurement curve of chlorine using G2CNP according to the method of the present invention.

In order to accomplish the above problem, the present inventors studied from various aspects to develop an ion measurement method which is unsusceptible to amylase in serum or urine and a reagent therefor, and finally found a novel system which is less susceptible to amylase in blood or urine while maintaining the reactivity to ions and thus completed the present invention.

Accordingly, the present inventors first found that the sensitivity to amylase is remarkably lowered (the reactivity to amylase is only 1/33 compared to 2-chloro-4-nitrophenyl maltotetraose, for example) by using 2-chloro-4-nitrophenyl maltose, and achieved the present invention on the basis of this novel finding.

The present invention is based on the basic technical idea of an enzyme assay of ions characterized by using maltose derivatives having a chromogenic group introduced into the reducing end. The present invention provides a system which allows the measurement of a specific type of ions under no influence of amylase brought from serum or the like and thus allows a convenient and exact measurement of a specific type of ions in various samples, especially samples even carrying amylase such as urine or serum samples.

The measurement reagent of the present invention comprises a maltose derivative having a chromogenic group introduced into the reducing end. The chromogenic group includes any chromophore which does not show absorption in the visible region when it is bound to maltose, but turns to show absorption in the visible region once it is released from maltose into a free state. Specific examples of such a chromophore include a phenyl group which may be substituted, such as 2-chloro-4-nitrophenyl group, paranitrophenyl group, 6-dichloro-4-nitrophenyl group, etc.

The maltose derivatives into which such a chromophore has been introduced includes, for example, 2-chloro-4-nitrophenyl maltose (hereinafter also referred to as "G2CNP"), of the structural formula shown by the following chemical formula 2:

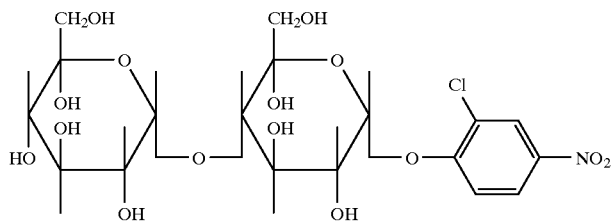

The maltose derivative shown by the formula 2 can be produced easily by those skilled in the art by referring to the descriptions of the following documents: Fathy A. M. "Neue Substrate zur Bestimmung und Charakterisiering von verschiedenen Hydrolasen" [Dissertation] Univ. of Freiburg F. R. G. and Emily S. Winn-Dean et al. (1988) Clin. Chem. 34, 10, 2005–2008.

One of important characteristics of the present invention is the employment of maltose derivatives having a chromogenic group such as G2CNP as a reagent for measuring amylase activity, and the present invention succeeds in remarkably lowering the reactivity to amylase than oligomers such as 2-chloro-4-nitrophenyl-α-D-maltotriose (G3CNP), -maltotetraose (G4CNP), -maltopentaose (G5CNP), -maltohexaose (G6CNP), -maltoheptaose (G7CNP), e.g. to 1/33 as compared with G4CNP while sufficiently maintaining the reactivity to ions by newly using such maltose derivatives.

Accordingly, the use of the above substrate allows exact measurement of a specific type of ions while avoiding the influence of amylase from samples.

The maltose derivatives such as G2CNP used in the present invention do not necessarily have a particularly high reactivity to α-amylase, unlike the reagents conventionally used for the measurement of α-amylase activity in the region of clinical tests. However, in the presence of a large amount of amylase, it is hydrolysed by amylase to increase the absorbance at 405 nm depending on the amount of a specific type of ions added or present in samples. The ions can be quantified by measuring the absorbance.

Therefore, any ion which can promote hydrolysis of maltose derivatives by amylase in a dose-dependent manner, can be measured by the measuring method of the present invention. Such ions include chlorine, calcium, for example.

The examples of the amylase which can be used in the present invention are amylases derived from porcine pancreas, Bacillus species, barley malt. The most preferable one is the porcine pancreas amylase. Such amylase proteins are commercially available from Sigma Chemical Company. Still, another kind amylase, which is activated in the presence of certain types of ions, may exist. It is within the scope of the present invention to measure the specific type of ions by using such amylase.

The amylase is used under the concentration of 10,000–500,000 units/ml, preferably, 50,000–200,000 units/ml in the mixture solution of the measurement reagent and the sample. This is significantly higher than the amount of amylase which is supposed to be contained in a biological samples, such as serum, urine, medulla fluid or the like, and therefore, the present method is able to measure a specific type of ions in such samples by excluding the effect of amylase contaminated in the sample.

The present invention further provides a method for measuring a specific type of ions which can promote hydrolysis of said maltose derivative in a dose-dependent manner. The measuring method of the present invention comprises reacting a sample which is supposed to contain a specific type of ions, and said measurement reagent under the existence of amylase, and measuring the concentration of the ions in said sample on the basis of quantity of free chromogenic group derived from the hydrolysis of the maltose derivative. The amount of color formation from the chromogenic group can be measured by applying light of an appropriate wavelength depending on the types of the chromogenic group.

Although the sequence for mixing a sample, the measurement reagent and amylase is not specifically restricted, the present method may be performed as follows, for example. First, to a sample such as serum, which has been diluted if necessary, amylase solution is added to the final concentration of about 10,000–500,000 units/ml, preferably, 50,000–200,000 units/ml, and reacted 20–40° C., preferably, 25–37° C. for 2–10 minutes, preferably, 5 minutes. Then, the solution of 1–10 mM, preferably, 3–6 mM of a maltose derivative, 2-chloro-4-nitrophenyl maltose, for example, is added and mixed, and the reaction mixture is warmed to 25–40° C., preferably, 37° C. The amount of variation of absorbance from the addition of the solution of maltose derivatives, is measured to calculate the amount of variation of absorbance per one minute as for one minute to three minutes, for example. This is compared to the amount of variation of absorbance in a standard curve which has been prepared as for samples containing a specific type of ions at a known concentration to measure the ion concentration in the sample.

The present invention further provides a kit for measuring a specific type of ions which can promote hydrolysis of said maltose derivative in a dose-dependent manner, comprising a maltose derivative, and also the amylase protein, buffer or the like, if necessary, which are packed appropriately. The kit of the present invention may further include a compound (solution) for drawing a standard curve.

This invention will now be illustrated by Examples, but it is not restricted to only these Examples.

EXAMPLE 1

Sample solutions, R-1 solution and R-2 solution were prepared as follows, respectively.

(Sample solutions): A series of sample solutions containing 100 mM, 50 mM, 25 mM, 12.5 mM, 6 mM, 3 mM, 1.5 mM and 0 mM NaCl were prepared in the presence of 5 mM calcium acetate.

(R-1 solution): A solution (1 ml) of commercially available porcine pancreas amylase in ammonium sulfate was centrifuged (10,000 rpm×5 min.), and the precipitated porcine pancreas amylase was collected and dissolved into 3 ml of 0.1M MES buffer (pH 6.0) containing 10 mM EDTA and the solution was allowed to stand at 4° C. for 30 minutes. Then, the buffer was replaced with 0.1M MES buffer (containing 0.1% BSA, 0.1% Triton X-405, 0.1% $NaN_3$; pH 6.0) in 60 ml Sephadex G-25 column to prepare a solution of porcine pancreas amylase free from chlorine and calcium. This solution is called as R-1 solution.

(R-2 solution): A 5 mM solution of 2-chloro-4-nitrophenyl maltose (kindly provided by Genzyme Corporation).

Each of the sample solutions (10 μl) was incubated with 300 μl of R-1 solution at 37° C. for 5 minutes, then thoroughly mixed with 100 μl of R-2 solution, and then the mixed solution as heated to 37° C. The amount of variation of absorbance at 405 nm from one minute to three minutes after the addition of R-2 solution was measured to calculate the amount of variation of absorbance per one minute. The measurement was carried out with Model 7150 automatic analyzer (Hitachi).

Assessment values were obtained by subtracting the amount of variation of absorbance observed with the sample solution containing 0 mM NaCl from the amount of variation of absorbance observed with the other sample solutions. The results are shown in FIG. 1.

Apparently from FIG. 1, the results confirmed that chlorine in samples can be measured with linear measurement curves by the method of the present invention.

EXAMPLE 2

The solutions R-1 and R-2 prepared in the above Example 1 were practically used for the measurement of chlorine in human serum. The results confirmed that chlorine in human serum samples can be measured by the method of the present invention.

EXAMPLE 3

Sample solutions, R-1 solution and R-2 solution were prepared as follows, respectively.

(Sample solutions): A series of sample solutions containing 5 mM, 2.5 mM, 1.25 mM, 0.625 mM, 0.3125 mM, 0.15 mM, 0.0075 mM and 0 mM calcium acetate were prepared in the presence of 100 mM NaCl.

R-1 solution and R-2 solution were prepared as described in Example 1.

Each of the sample solutions (10 μl) was incubated with 300 μl of R-1 solution at 37° C. for 5 minutes, then thoroughly mixed with 100 μl of R-2 solution, and then the mixed solution as heated to 37° C. The amount of variation of absorbance at 405 nm from one minute to three minutes after the addition of R-2 solution was measured to calculate the amount of variation of absorbance per one minute. The measurement was carried out with Model 7150 automatic analyzer (Hitachi).

Assessment values were obtained by subtracting the amount of variation of absorbance observed with the sample solution containing 0 mM NaCl from the amount of variation of absorbance observed with the other sample solutions. The results are shown in FIG. 2.

Figure 2:
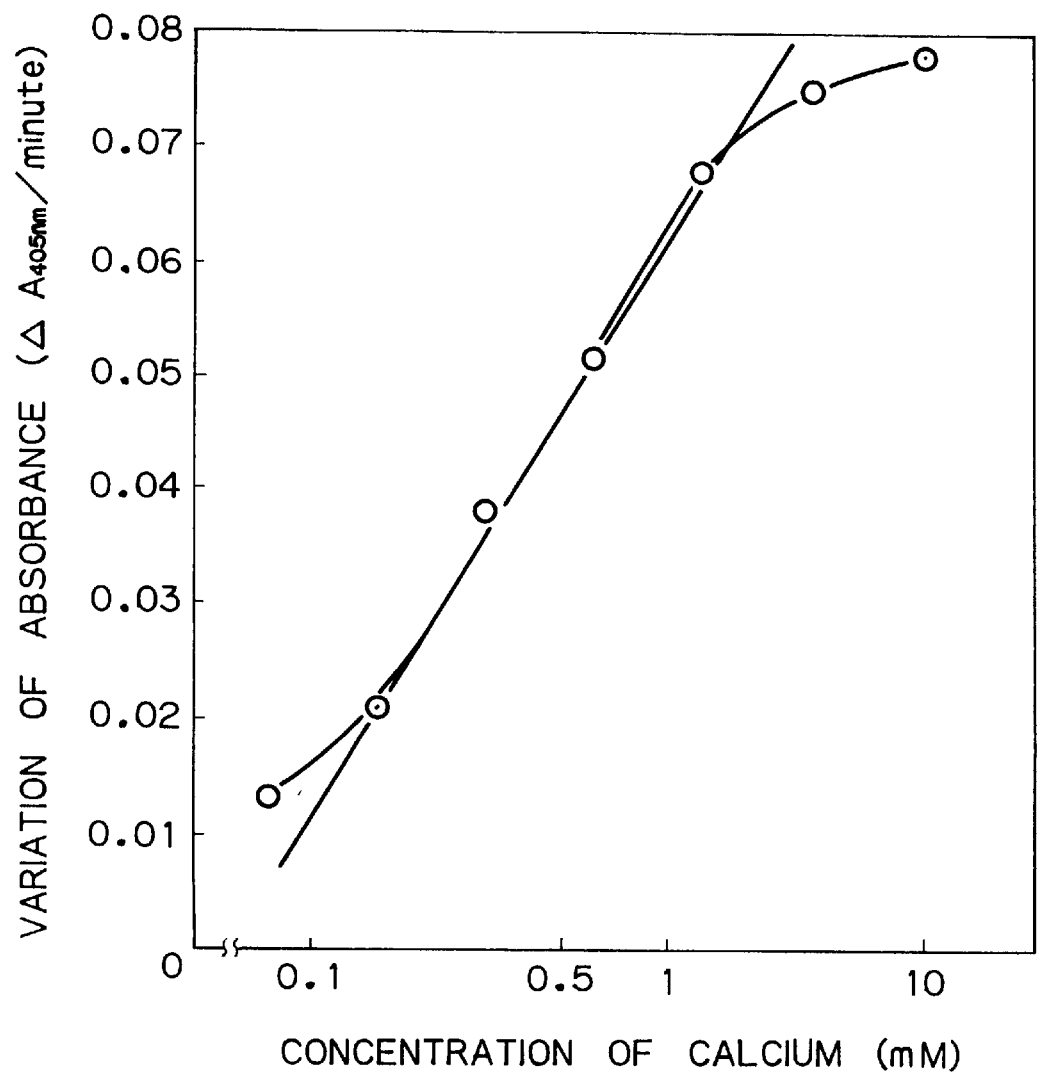
FIG. 2 shows a measurement curve of calcium using G2CNP according to the method of the present invention.

Apparently from FIG. 2, the results confirmed that calcium in samples can be measured with linear measurement curves by the method of the present invention.

EXAMPLE 4

The solutions R-1 and R-2 prepared in the above Example 3 were practically used for the measurement of calcium in human serum. The results confirmed that calcium in human serum samples can be measured by the method of the present invention.

EXAMPLE 5

Preparation of 2-chloro-4-nitrophenyl maltose

According to the method of the present invention, specific types of ions can be conveniently, rapidly and exactly measured under no influence of amylase coming from samples. Accordingly, the present invention allows a rapid and exact measurement of the ions in ordinary samples as well as various biological samples such as serum or urine without needing any skill, and thus greatly contributes to, for example, clinical diagnosis.

What is claimed is:

1. A method of measuring concentration of chlorine ions or calcium ions in a sample, said method comprising the steps of:

(a) contacting in the presence of amylase a sample containing chlorine ions or calcium ions with a reagent of the formula:

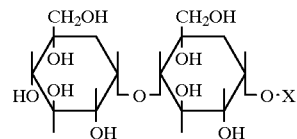

wherein X is a phenyl or substituted phenyl chromophore, whereby chlorine or calcium ions hydrolyze said reagent and release said chromophore;

(b) determining the quantity of chromophore released in step (a); and (c) correlating the quantity of released chromophore measured in step (b) to the concentration of chlorine ions or calcium ions in the sample.

2. The method of claim 1 in which the chromophore is 2-chloro-4-nitrophenyl, paranitrophenyl or 6-dichloro-4-nitrophenyl.

3. A reagent for measuring concentration of chlorine ions or calcium ions comprising a maltose derivative of the formula:

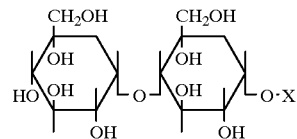

wherein X is a phenyl or substituted phenyl chromophore in which chlorine ions or calcium ions promote hydrolysis of said maltose derivative.

4. The reagent of claim 3 in which the chromophore is 2-chloro-4-nitrophenyl, paranitrophenyl, or 6-dichloro-4-nitrophenyl.

* * * * *